(12) United States Patent
Hansson et al.

(10) Patent No.: US 9,101,420 B2
(45) Date of Patent: Aug. 11, 2015

(54) DEVICE FOR FIXATION OF BONE FRAGMENTS AT BONE FRACTURES

(75) Inventors: Henrik Hansson, Vreta Kloster (SE); Lars Oster, Lidkoping (SE)

(73) Assignee: SWEMAC INNOVATION AB, Linkoping (SE)

( * ) Notice: Subject to any disclaimer, the term of this patent is extended or adjusted under 35 U.S.C. 154(b) by 490 days.

(21) Appl. No.: 12/934,274

(22) PCT Filed: Mar. 25, 2009

(86) PCT No.: PCT/SE2009/050314
§ 371 (c)(1),
(2), (4) Date: Dec. 14, 2010

(87) PCT Pub. No.: WO2009/120142
PCT Pub. Date: Oct. 1, 2009

(65) Prior Publication Data
US 2011/0264150 A1    Oct. 27, 2011

(30) Foreign Application Priority Data
Mar. 27, 2008    (SE) ...................................... 0800679

(51) Int. Cl.
*A61B 17/80*    (2006.01)
*A61B 17/74*    (2006.01)
(Continued)

(52) U.S. Cl.
CPC ........... *A61B 17/746* (2013.01); *A61B 17/8042* (2013.01); *A61B 17/86* (2013.01); *A61B 2019/461* (2013.01)

(58) Field of Classification Search
CPC ........... A61B 17/8047; A61B 17/7059; A61B 17/8042; A61B 17/8605; A61B 17/1728
USPC ...................... 606/64–67, 280–299, 105, 319
See application file for complete search history.

(56) References Cited

U.S. PATENT DOCUMENTS 5,976,139 A * 11/1999 Bramlet .......................... 606/66
6,890,333 B2 * 5/2005 von Hoffmann et al. ....... 606/67
(Continued)

FOREIGN PATENT DOCUMENTS

EP    1 488 754    12/2004
JP    2002-515800    5/2002
(Continued)

*Primary Examiner* — Andrew Yang
*Assistant Examiner* — Diana S Jones
(74) *Attorney, Agent, or Firm* — Tarolli, Sundheim, Covell & Tummino LLP

(57) ABSTRACT

A device for fixation of bone fragments at bone fractures including at least two fixation means (5, 6), a securing plate (4) and at least one securing means (23) for the fixation means. Each fixation means (5, 6) has a first fixing portion (19) for fixing the fixation means in an inner bone fragment (3), a second fixing portion (21) which serves in conjunction with the securing means (23) for locking the fixation means in a hole (9) which runs through the securing plate (4) disposed on the outside of an outer bone fragment (2) and allowing movement of the outer bone fragment relative to it, so that the fixation means are prevented from changing their angular position relative to the securing plate and relative to one another, and a middle portion (22) which is situated between the fixing portions (19, 21) and runs through the outer bone fragment (2), along which middle portion the outer bone fragment can slide inwards towards the inner bone fragment (3) in which the fixation means is fixed, and the securing means (23) has an external thread for screwing it firmly into a hole (9) in the securing plate (4).

18 Claims, 15 Drawing Sheets

(51) Int. Cl.
  *A61B 17/86* (2006.01)
  *A61B 19/00* (2006.01)

(56) References Cited

U.S. PATENT DOCUMENTS

| | | | |
|---|---|---|---|
| 6,902,567 B2 * | 6/2005 | Del Medico | 606/71 |
| 2002/0183756 A1 | 12/2002 | Michelson | |
| 2003/0171754 A1 | 9/2003 | Del Medico | |
| 2004/0193162 A1 | 9/2004 | Bramlet et al. | |
| 2004/0220572 A1 | 11/2004 | Michelson | |
| 2005/0234457 A1 * | 10/2005 | James et al. | 606/69 |
| 2006/0195104 A1 | 8/2006 | Schlafli et al. | |
| 2007/0055248 A1 | 3/2007 | Zlowodzki et al. | |
| 2009/0254089 A1 * | 10/2009 | Tipirneni et al. | 606/64 |
| 2013/0013002 A1 | 1/2013 | Michelson | |

FOREIGN PATENT DOCUMENTS

| | | |
|---|---|---|
| JP | 2006-81914 | 3/2006 |
| WO | 2004/075766 | 9/2004 |
| WO | WO-2004/075766 A1 | 9/2004 |
| WO | 2007/123655 | 11/2007 |

* cited by examiner

DEVICE FOR FIXATION OF BONE FRAGMENTS AT BONE FRACTURES

BACKGROUND TO THE INVENTION

The present invention relates to a device for fixation of bone fragments at bone fractures.

After a bone fracture such as a femur neck fracture, the bone fragments at the fracture need fixing. This is currently done by using suitable fixation means, e.g. bone nails or bone screws.

After the completion of surgery, even as early as when the effects of the anaesthesia have passed and the patient is still confined to bed, but above all when the patient is beginning to be up and walk and stand on the leg, the fixed bone fragments and the fixation means are subject to large forces, particularly to rotational forces acting downwards and rearwards.

The fixation means alone are often insufficient to counteract these rotational forces and the bone fragments have to be used to help to lock the fracture. If this is not done and the bone fragments are caused to rotate relative to one another by said forces, the result will be shifting of the angular positions of the fixation means to such an extent that they risk substantially crossing one another, thereby keeping the fracture parted and preventing healing.

BRIEF SUMMARY OF THE INVENTION

The object of the present invention is accordingly to prevent or counteract this and therefore configure the device in such a way that the fixation means are not allowed to rotate and cross one another.

To this end, the device according to the invention is characterised in that it comprises at least two fixation means, a securing plate and at least one securing means for the fixation means, that each fixation means has a first fixing portion for fixing the fixation means in an inner bone fragment, a second fixing portion to serve in conjunction with the securing means for locking the fixation means in a hole which runs through the securing plate disposed on the outside of an outer bone fragment and allowing movement of the outer bone fragment relative to it, so that the fixation means are prevented from changing their angular position relative to the securing plate and relative to one another, and a middle portion which is situated between the fixing portions and runs through the outer bone fragment, along which middle portion the outer bone fragment can slide inwards towards the inner bone fragment in which the fixation means are fixed, and that the securing means has an external thread for screwing it firmly into a hole in the securing plate.

The result of the fixation means being thus fixed to the inner bone fragment and to the securing plate while the outer bone fragment can move towards the inner bone fragment and, in so doing, be guided by the fixation means is that the bone fragments are kept fixed but compression of the bone fragments is nevertheless allowed, the device and the bone fragments thus being able to absorb the aforesaid rotational forces and control them so that no redislocation occurs. The fixing of the fixation means in the inner bone fragment and the locking of the fixation means to the securing plate also reduce the risk of screws loosening in cases where the fixation means take the form of bone screws.

Other objects and advantages of the invention will be apparent to one skilled in the art who examines the attached drawings and the following detailed description of preferred embodiments of and method for fitting the device according to the invention.

DETAILED DESCRIPTION OF PREFERRED EMBODIMENTS OF THE INVENTION

Figure 1:
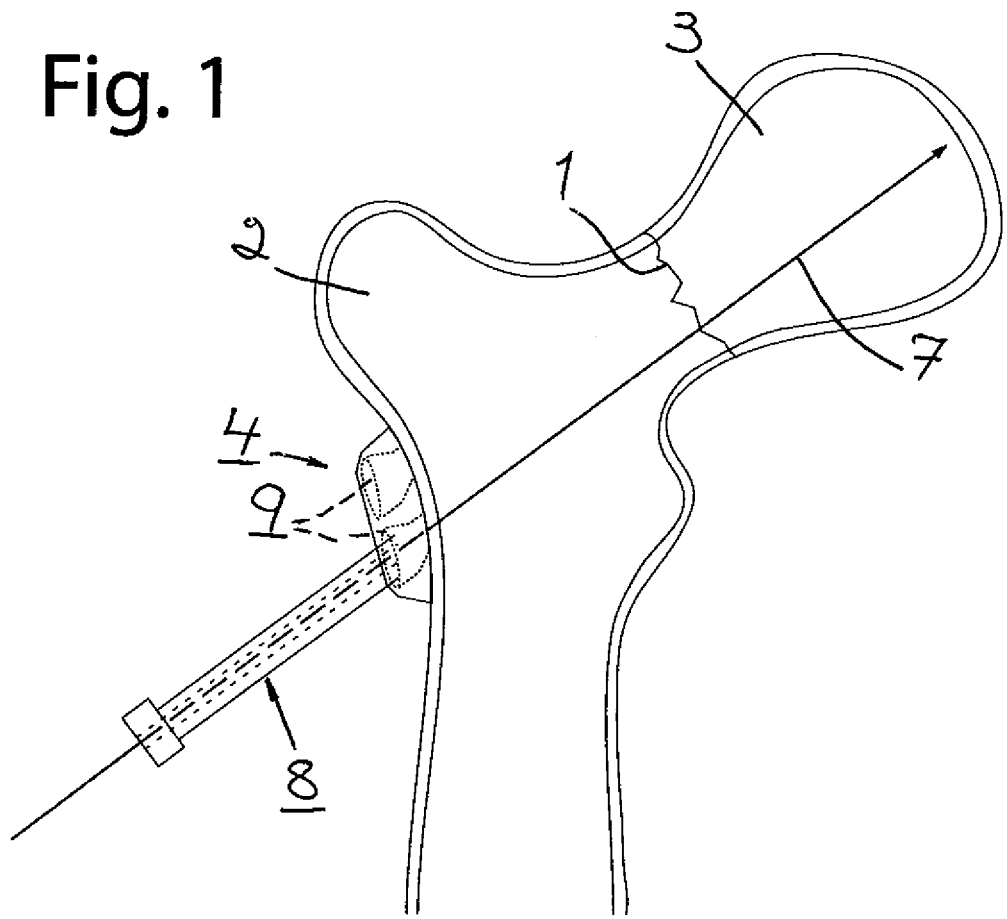
FIG. 1 illustrates in side view upper portions of a femur with a femur neck fracture and a device according to the present invention, showing a securing plate and a first guide sleeve usable in conjunction with said plate for guiding a guide wire drilled into bone fragments which are to be fixed on their respective sides of the fracture.
Figure 2:
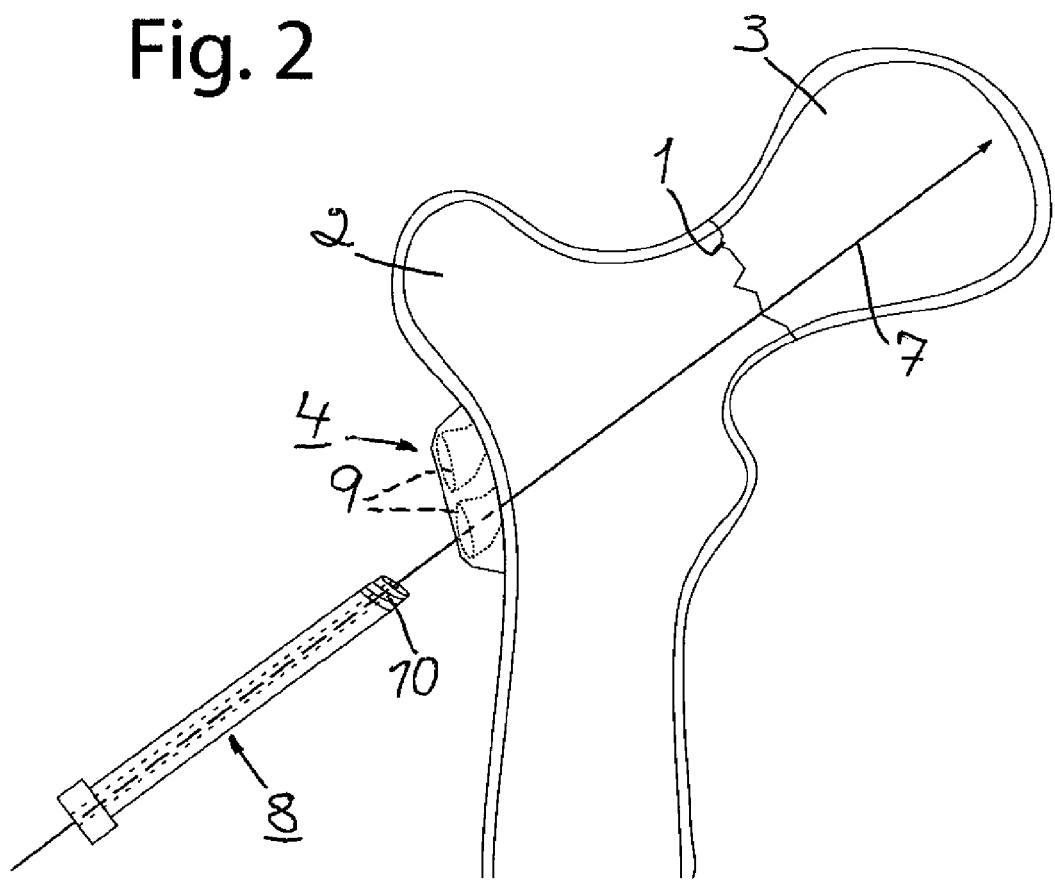
FIG. 2 illustrates in side view the removal of the guide sleeve for the guide wire.
Figure 9:
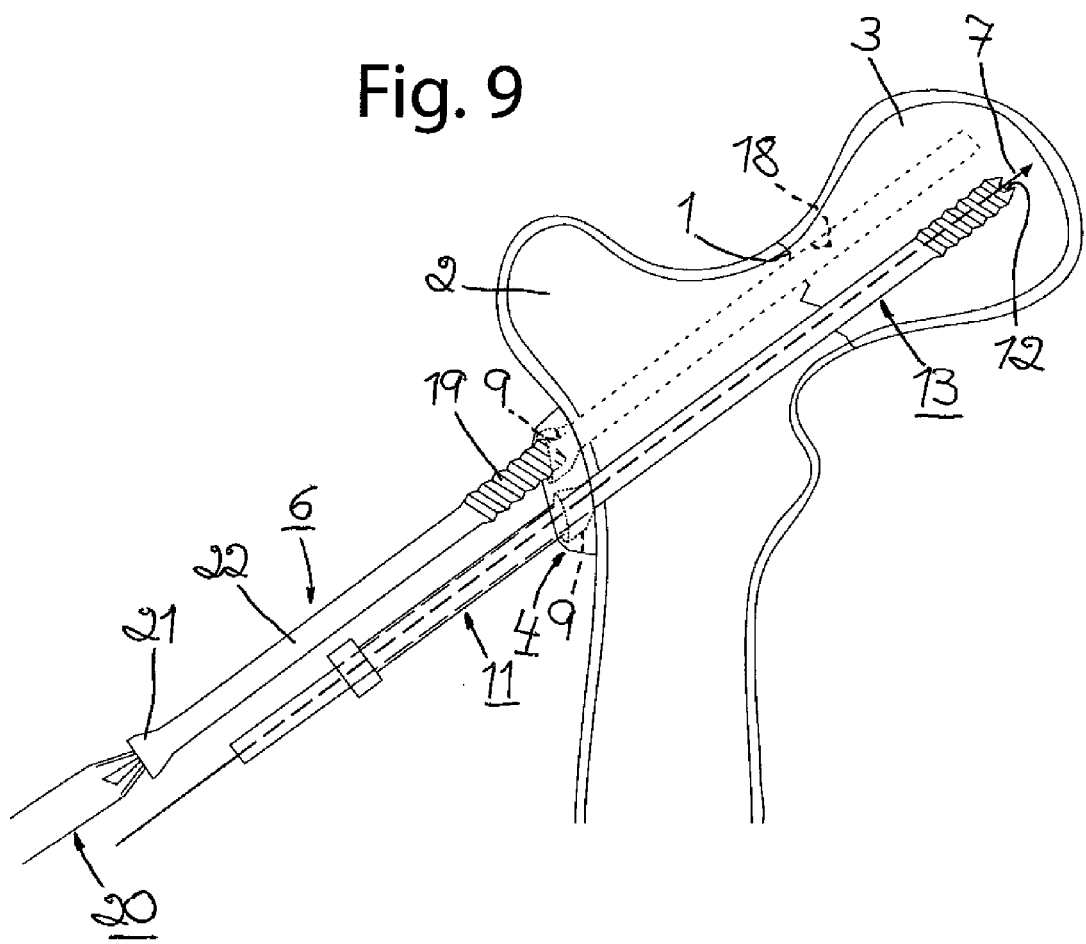
FIG. 9 depicts in side view the application of a fixation means in the form of a bone screw in the securing plate for further screwing of the bone screw into the second hole in the bone fragments.

The drawings illustrate one of several possible methods for fixation of a fracture at the neck of a femur by means of a device according to the present invention. As previously indicated, FIG. 1 depicts upper portions of a femur with a femur neck fracture 1, and an outer bone fragment 2 and an inner bone fragment 3 on their respective sides of the fracture. A securing plate 4, which forms part of the device according to the present invention, for fixation means in the form of bone screws or bone nails, in the version depicted two substantially parallel bone screws 5, 6 (see FIGS. 9-11) for fixing the bone fragments 2, 3, is disposed on the outside of the outer bone fragment 2. The respective bone screws 5, 6 are preferably integral. The securing plate 4 is so arranged that it allows movement of the outer bone fragment 2 relative to it, i.e. it is not connected to the outer bone fragment nor disposed in some other way whereby it would move with the latter upon compression of the bone fragments 2, 3. In the femur, a guide wire 7 with a diameter of preferably about 2.4 mm has been drilled through the outer bone fragment 2 and into the inner bone fragment 3 under radioscopy and with guidance by a guide sleeve 8 with an inside diameter of preferably about 2.5 mm. The guide wire 7 is intended to guide a drill for drilling a hole for the bone screw 5 in the bone fragments 2, 3. According to the invention, the guide sleeve 8 for the guide wire 7 is applied in the securing plate 4, preferably by being screwed firmly into an, in the embodiment depicted, at least partly threaded hole 9 running through the plate, and has for the purpose an externally threaded forward end portion 10 (see FIG. 2 depicting the guide sleeve 8 when it has been unscrewed from the plate 4). This externally threaded forward end portion 10 does of course have an outside diameter corresponding to the diameter of the threaded portion 9a of the at least partly threaded hole 9 in the securing plate 4, i.e. preferably about 9-10 mm.

Figure 3:
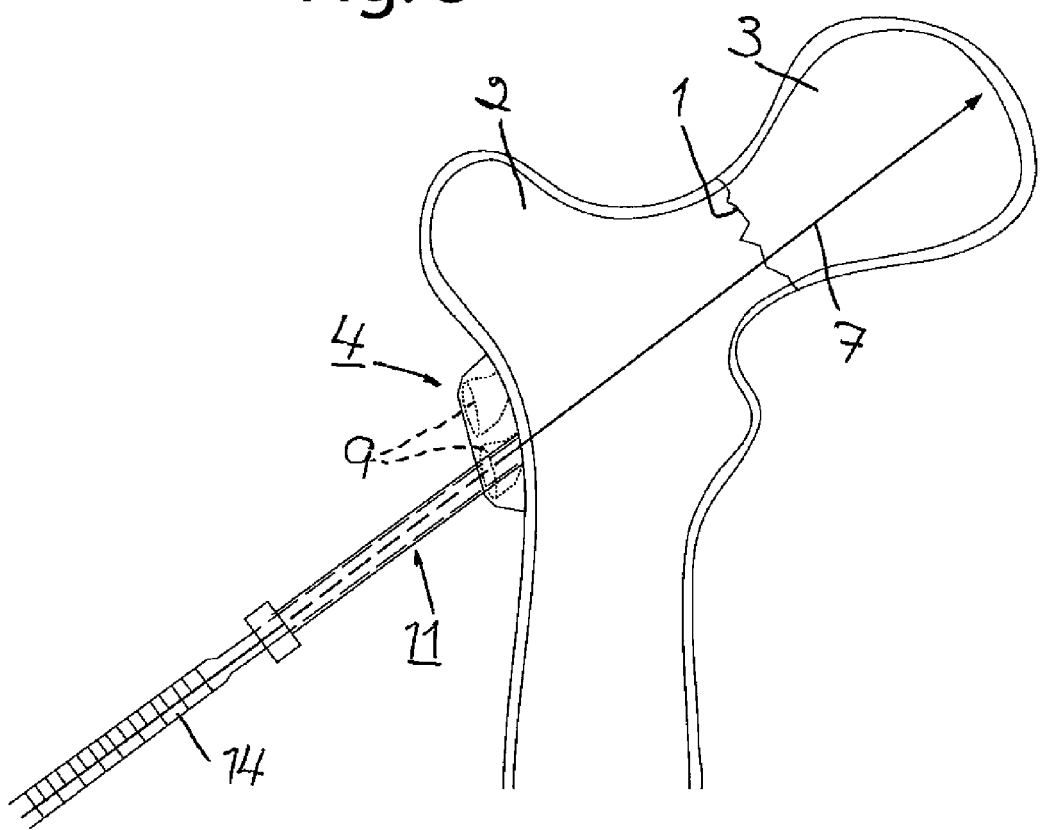
FIG. 3 illustrates in side view a second guide sleeve for guiding a drill, and a gauge rod for determining how long the fixation means should be.
Figure 4:
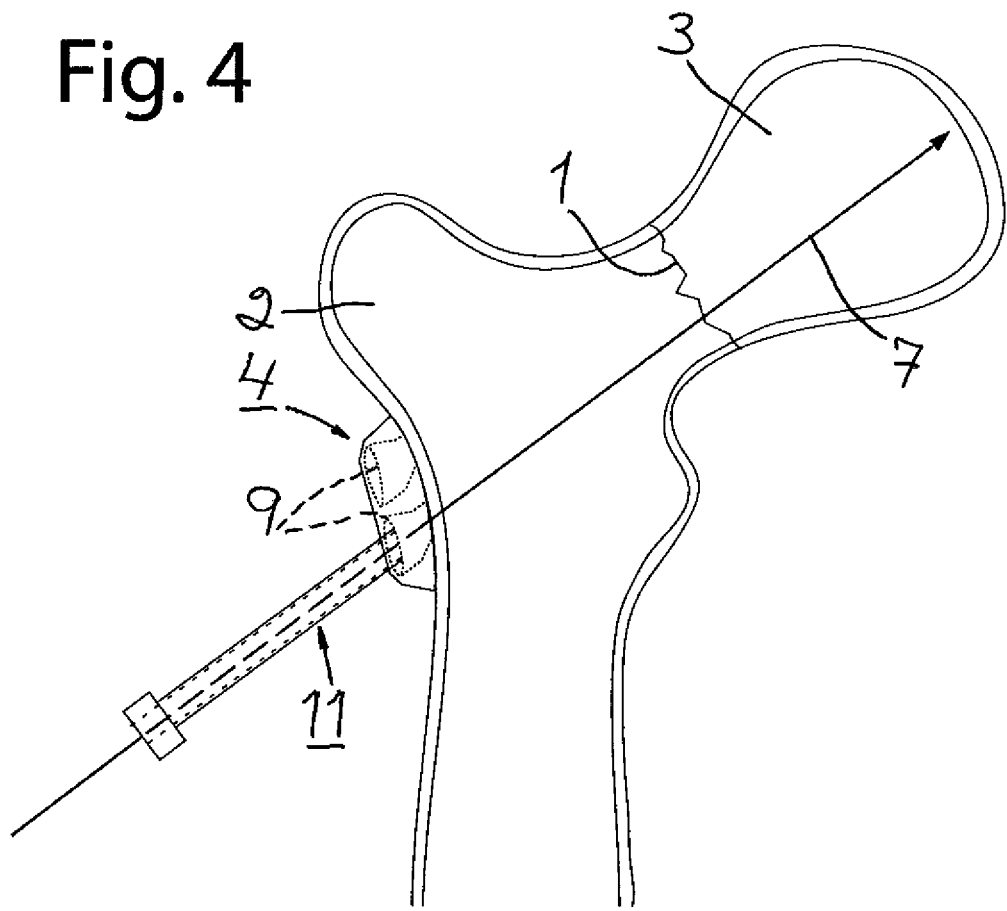
FIG. 4 depicts in side view the second guide sleeve after removal of the gauge rod.

After the removal of the guide sleeve 8 for the guide wire 7, a second guide sleeve 11, with an inside diameter of preferably about 6.5 mm and an externally threaded forward portion with the same outside diameter as the first guide sleeve, is applied in, i.e. screwed into, the threaded portion 9a of the at least partly threaded hole 9 in the securing plate 4 (FIG. 3). This guide sleeve 11 is intended to guide a drill 13, which has running through it a duct 12 for the wire guide 7 (see FIGS. 5-10), in order to drill the hole for the bone screw 5 in the bone fragments 2, 3. When the second guide sleeve 11 has been applied to the securing plate 4, a gauge rod 14 is inserted at the rear of this guide sleeve and through the sleeve towards the bone 2, 3. The gauge rod 14 can be used in a conventional manner to indicate how far the drilling should go or how long the bone screw 5 should be for optimum function. In FIG. 4 the gauge rod 14 has been removed.

Figure 5:
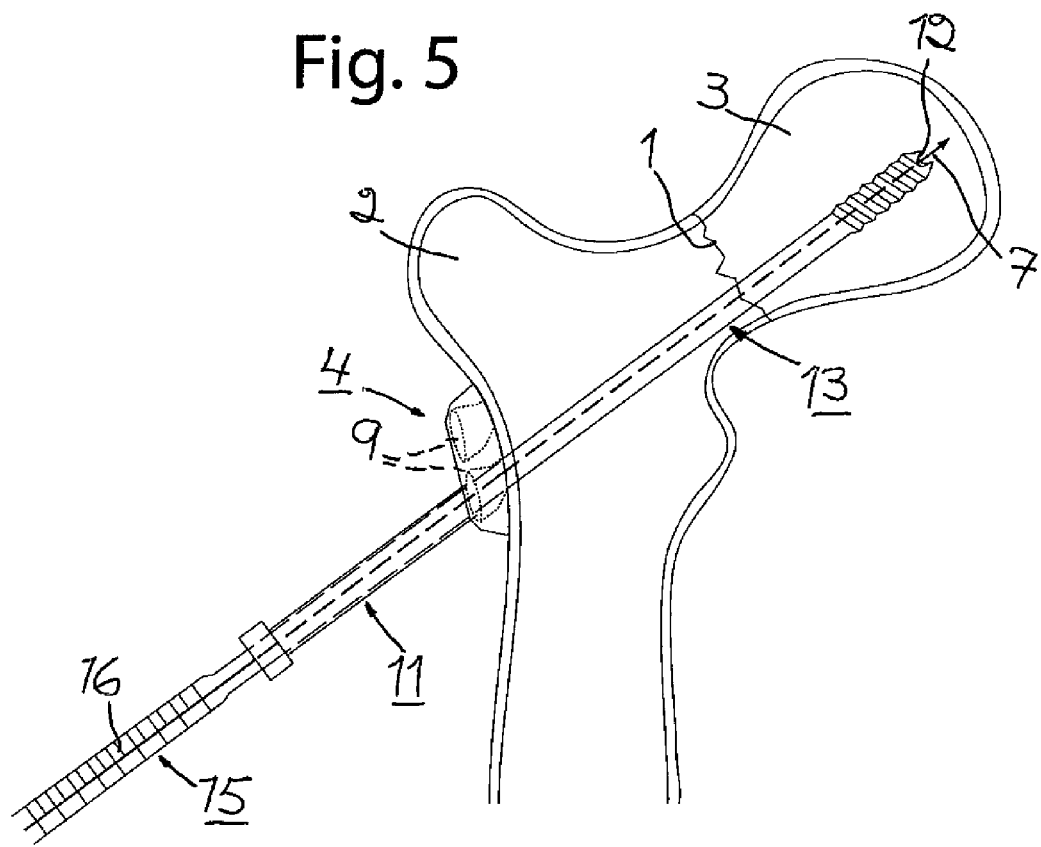
FIG. 5 illustrates in side view the insertion in the second guide sleeve of a drill, provided with a duct, for drilling a hole for a fixation means in the form of a bone screw and for drilling the hole for said bone screw in the bone fragments.

The hole for the bone screw 5 can now be drilled. Accordingly, as illustrated in FIG. 5, the drill 13 provided with the duct 12 is introduced through the guide sleeve 11 towards the bone fragment 2 and the drilling of the hole for the bone screw 5 is commenced, using a suitable drive device 15. The drill 13 has an outside diameter of preferably about 6.5 mm and fits exactly in the guide sleeve 11. The drill 13 is guided by the guide sleeve 11 to correct position against the bone fragment 2 and thereafter by the guide wire 7 through the bone fragment 2 and past the fracture 1 into the bone fragment 3. Monitoring that the hole for the bone screw 5 is of correct length is carried out with advantage at the rear of the guide sleeve 11, where the drill 13 or the drive device 15 bears suitable markings 16. This entails the drill 13 being halted about 2 cm from the tip of the guide wire 7, i.e. about 2 cm before reaching the point to which the bone screw 5 is intended to be screwed in.

Figure 6:
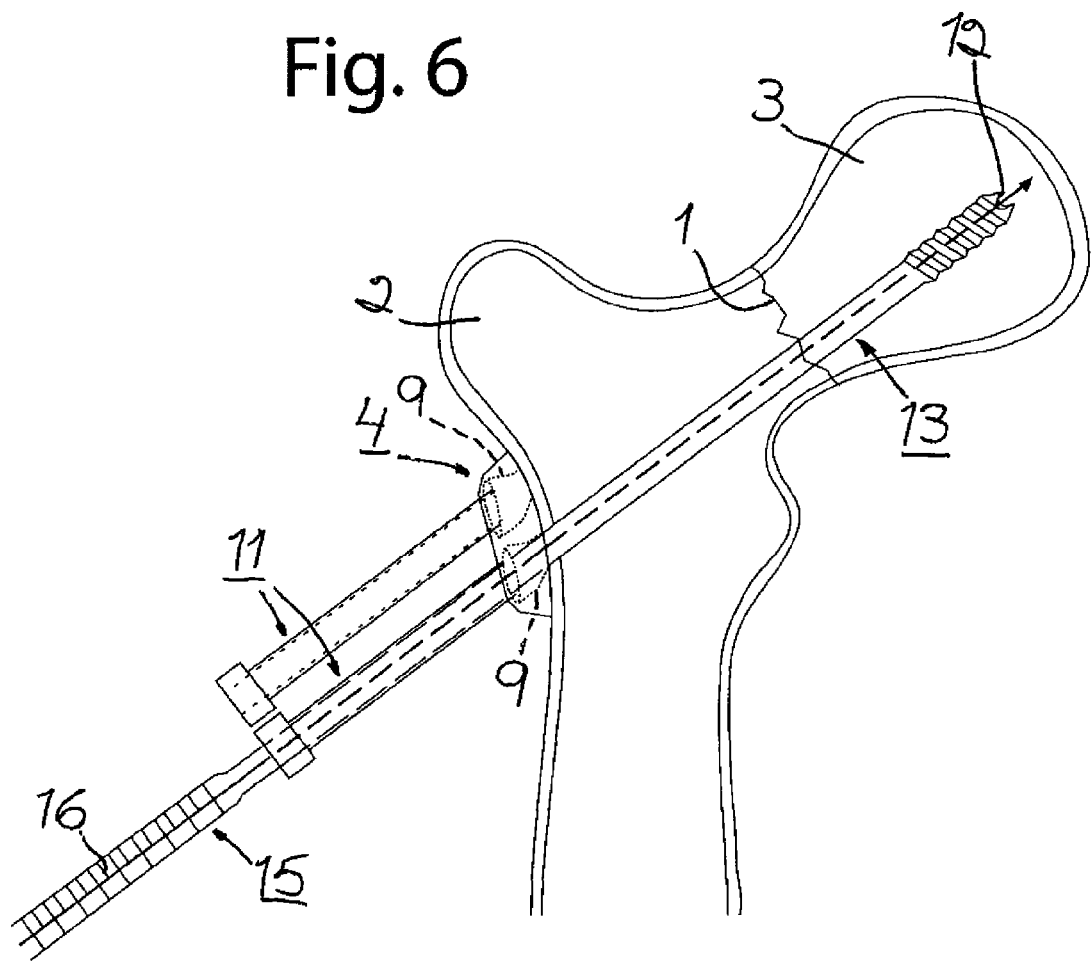
FIG. 6 depicts in side view the application of a further second guide sleeve for guiding a drill in the securing plate.
Figure 7:
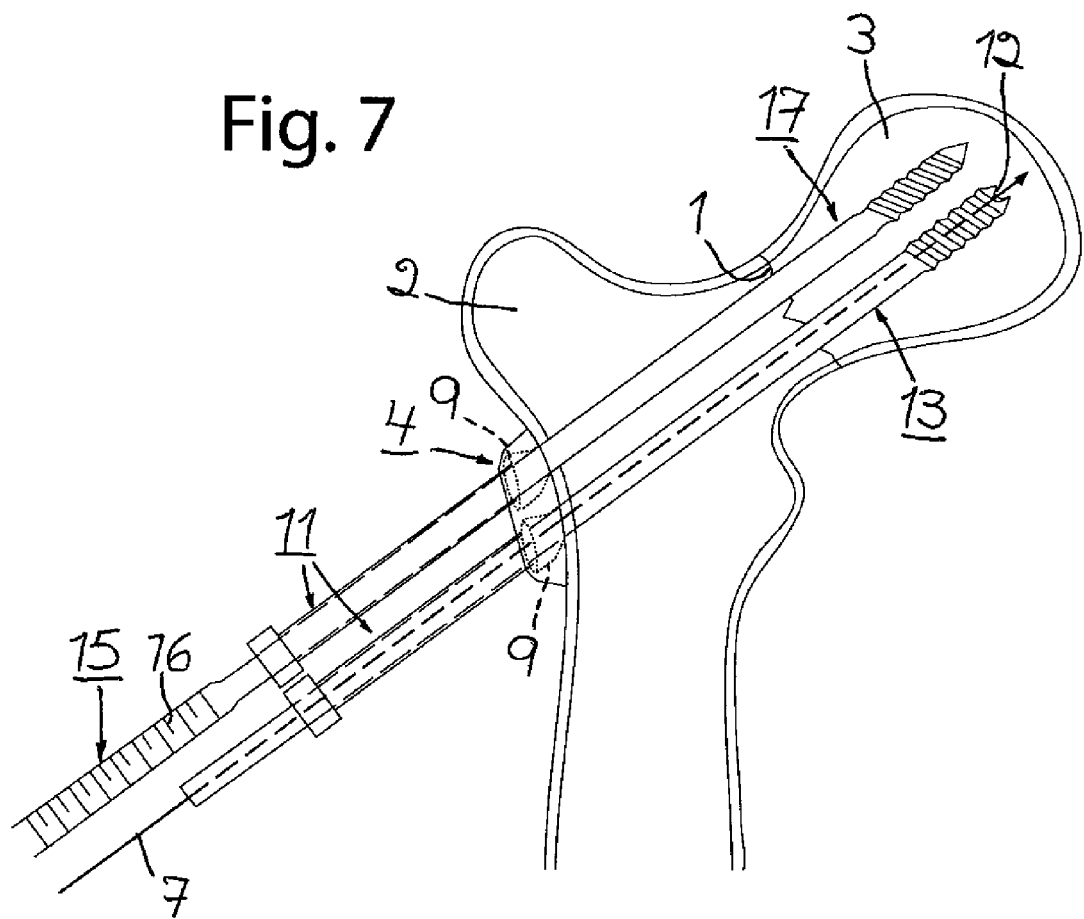
FIG. 7 illustrates in side view the further second guide sleeve after application of a drill with a cone-shaped tip therein and drilling of a second hole for a bone screw in the bone fragments.
Figure 8:
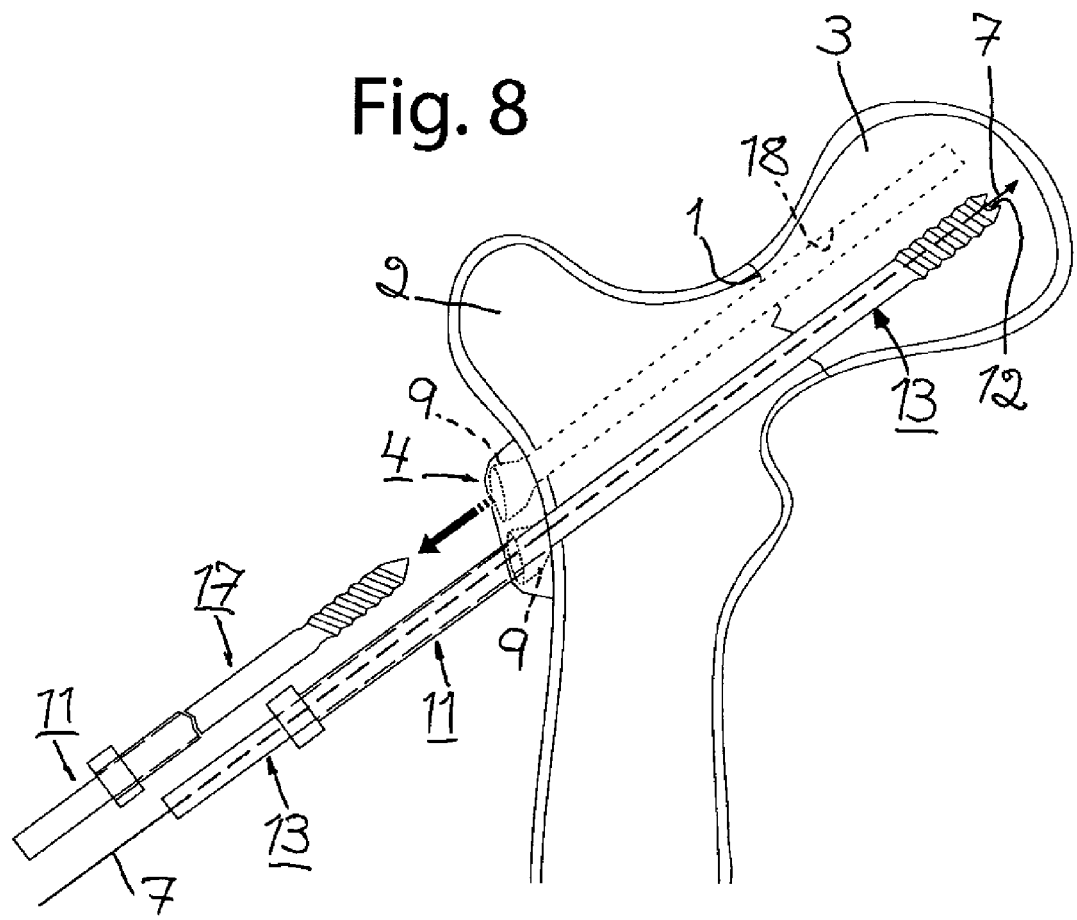
FIG. 8 illustrates in side view the removal of the further second guide sleeve and the respective drill.

After any necessary adjustment of the securing plate 4 sideways, a further second guide sleeve 11 is now applied as per FIG. 6 in a second at least partly threaded hole 9 running through the plate. Alternatively, a guide sleeve 8 for a guide wire 7 may be applied first and the same procedure as before, using the same items as above, may be carried out. With advantage, although not depicted in the drawings, guide sleeves of a desired kind 8, 11 may already from the outset be applied in respective at least partly threaded holes 9 in the securing plate 4 to give the surgeon a better grip for correct control of the guide wire 7 and respective drills 13, 17. The guide sleeve 11 in the version depicted is intended to guide a drill 17 without a duct for the guide wire but with a cone-shaped tip (see FIG. 7). This solid drill 17 is drilled in to desired position for the bone screw 6 by means of the drive device 15. Correct length is read with advantage at the rear of the guide sleeve 11, where the drill 17 or the drive device 15 bears suitable markings 16 (FIG. 7). The drill 17 and the guide sleeve 11 for it are removed (FIG. 8), leaving for the bone screw 6 a hole 18 in the bone fragments 2, 3 which is shorter than the distance to which the bone screw is intended to be screwed in.

Figure 10:
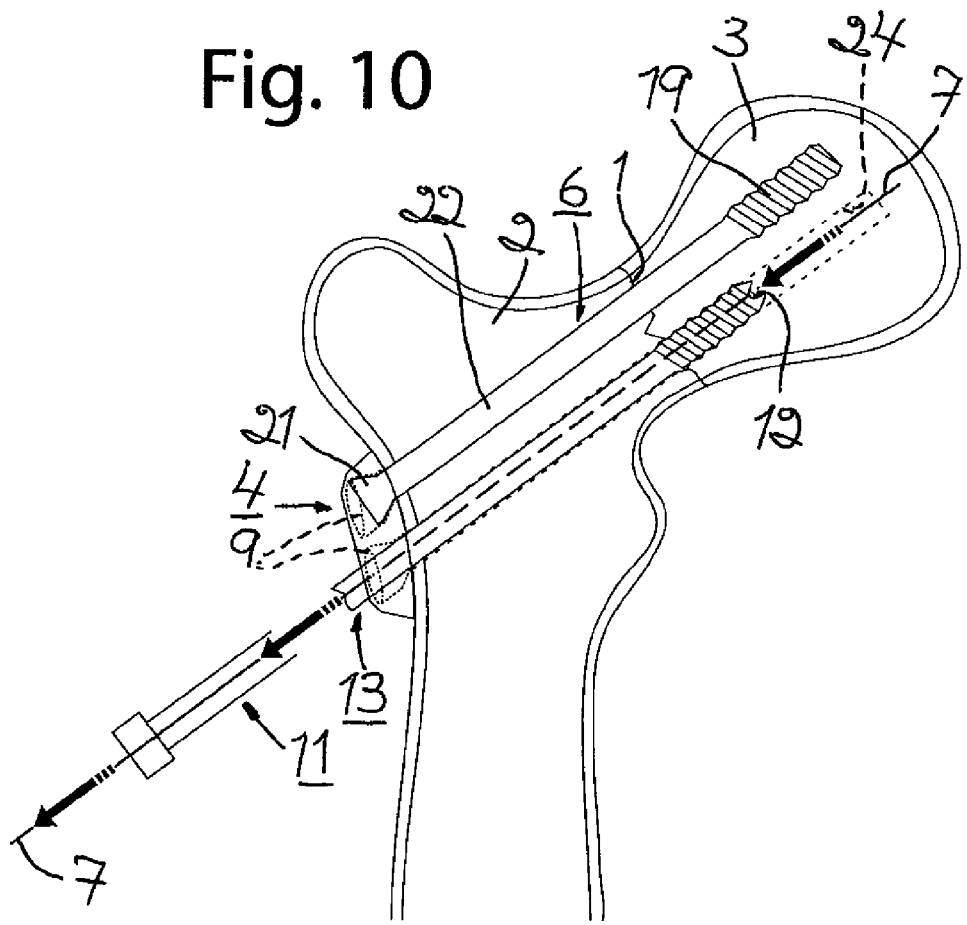
FIG. 10 illustrates in side view the bone screw when it has been screwed into the bone fragments.

The bone screw 6 can now, by means of a first fixing portion in the form of a threaded forward end portion 19, be inserted in through the at least partly threaded clear hole 9 in the securing plate 4 (see FIG. 9) and be screwed into the hole 18 in the bone fragments 2, 3 in order to fix these bone fragments. This is effected without the threaded forward end portion 19 of the bone screw 6 cooperating with the thread in the threaded portion 9a of the at least partly threaded hole 9 in the plate 4. For example, the thread on the threaded forward end portion 19 of the bone screw 6 may be about 8 mm, while the thread in the at least partly threaded hole 9 in the securing plate 4 may, as previously indicated, be about 9-10 mm. The bone screw 6 is screwed in by using a suitable tool, in the version depicted a suitable type of screwdriver 20. Alternatively it is of course possible to conceive of using for this purpose the same drive device 15 as for the drills 13, 17. The bone screw 6 is screwed in until a second fixing portion in the form of a unthreaded rear end portion 21 thereof which narrows conically in the screwing-in direction of the bone screw cooperates with, preferably abuts against, a corresponding conically narrowing unthreaded portion 9b of the at least partly threaded hole 9 in the securing plate 4, while at the same time the threaded forward portion 19 of the bone screw is screwed through the outer bone fragment 2 and into the inner bone fragment 3 for engagement therein and locking of this latter bone fragment to the bone screw. The conically narrowing end portion 21 of the bone screw 6 preferably narrows from about 9-10 mm to about 6.5 mm in the screwing-in direction of the bone screw. The middle portion 22 of the bone screw 6, which is preferably unthreaded, has with advantage an outside diameter corresponding to that of the drill 17, i.e. about 6.5 mm. In FIG. 10 the bone screw 6 is fully screwed in. A securing means 23 (FIGS. 11-14) for the bone screw is screwed firmly into the threaded portion 9a of the at least partly threaded hole 9 in order to press the bone screw against, and hence lock it to, the securing plate 4, and hence also lock the inner bone fragment 3 to the plate, and to lock the outer bone fragment 2 between the plate and the inner bone fragment. This is best illustrated in FIGS. 11 and 12.

Figure 11:
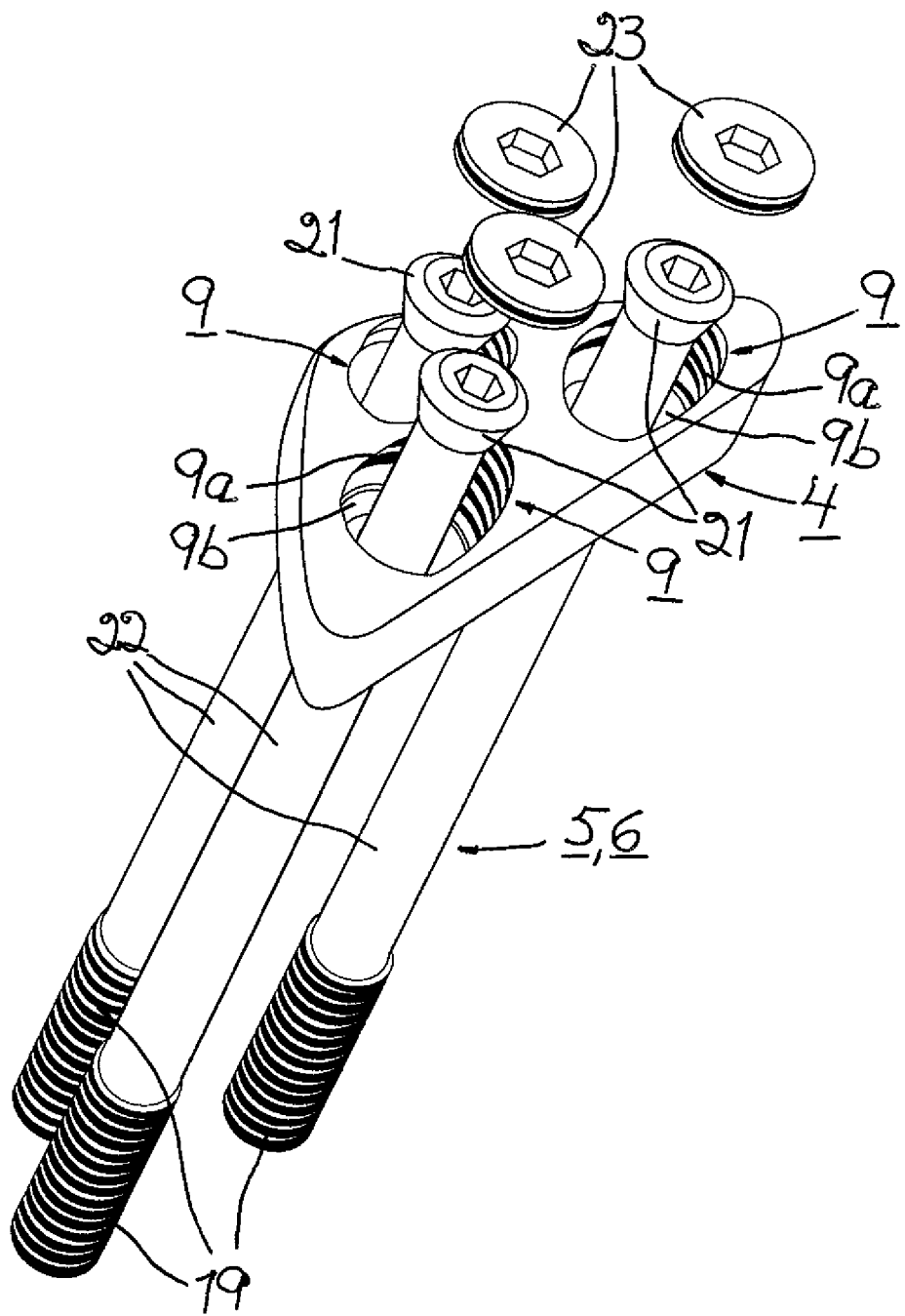
FIG. 11 illustrates in exploded view in perspective a preferred embodiment of the device according to the present invention, comprising three bone screws, a securing plate and securing means in the form of lock washers for the bone screws.
Figure 12:
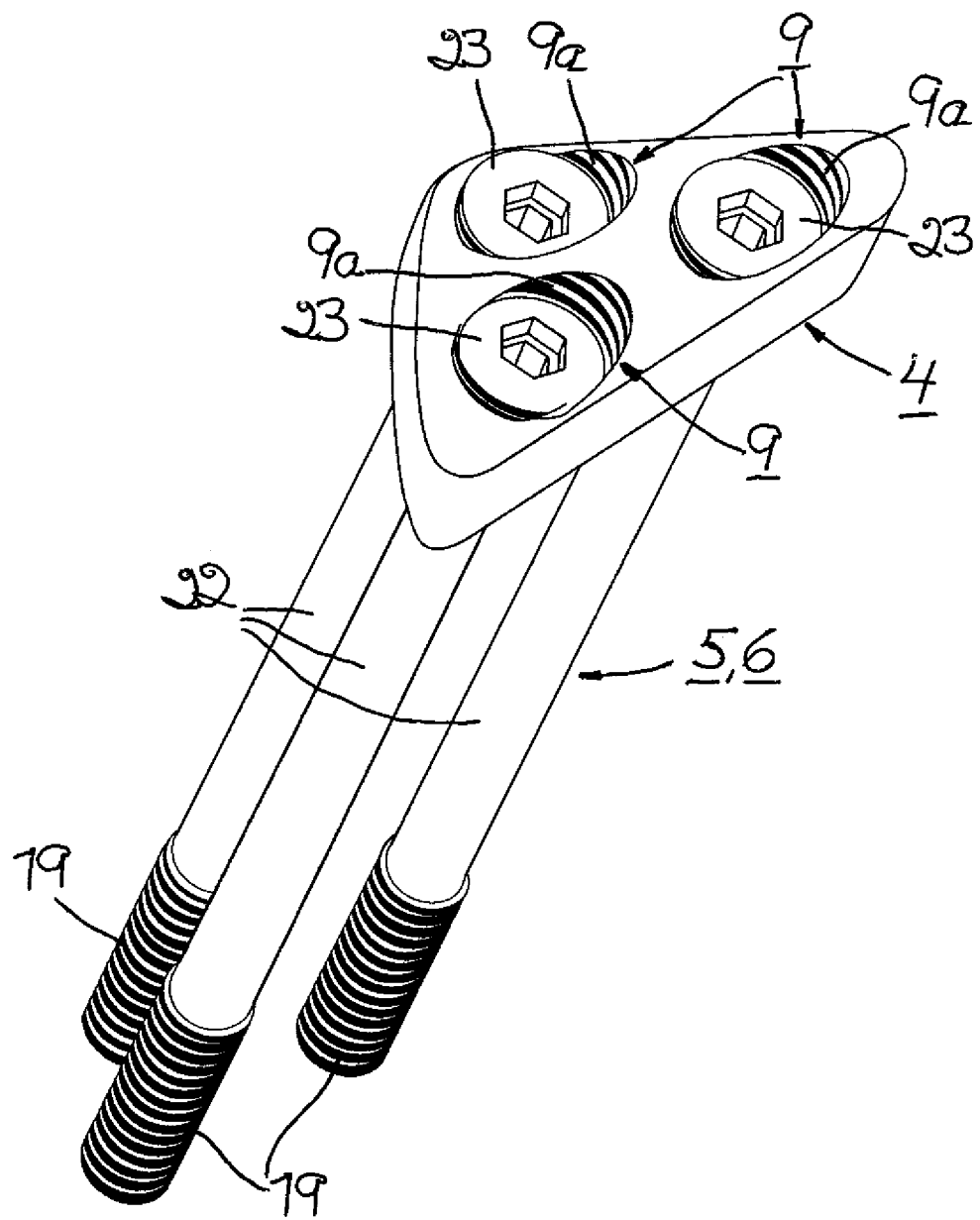
FIG. 12 illustrates in perspective view the device according to FIG. 11 after assembly.

FIGS. 11 and 12 illustrate a preferred embodiment of the device according to the present invention. The device comprises here a securing plate 4, three fixation means in the form of bone screws 5 and/or 6 and a securing means 23 for each bone screw. FIG. 11 depicts the device in exploded view, before assembly, whereas FIG. 12 depicts the device after assembly.

Figure 13:
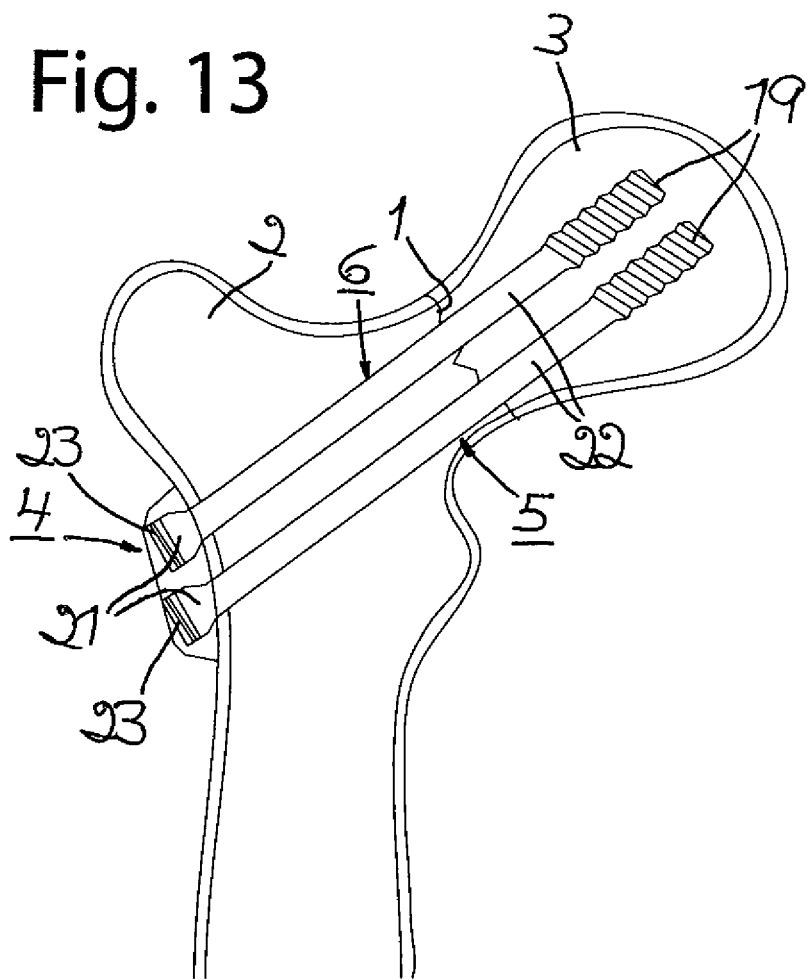
FIG. 13 depicts in side view a second bone screw screwed into the first hole in the bone fragments after the guide wire, drill and guide sleeve have been removed.
Figure 14:
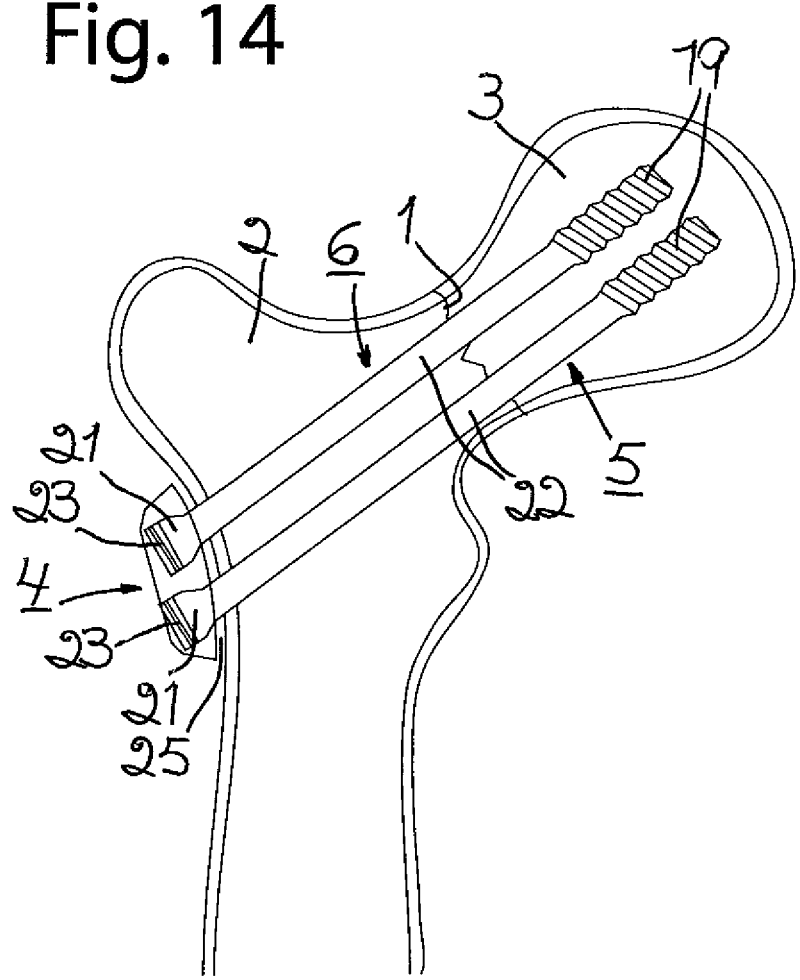
FIG. 14 illustrates in an alternative position the securing plate with bone screws locked in the plate by the securing means; and lastly

In FIG. 13, the drill 13, the guide sleeve 11 for the drill, and the guide wire 7 have been removed. The bone screw 5, preferably similar in form to the bone screw 6, is introduced into the at least partly threaded hole 9 in the plate 4 vacated by the removal of said items and into the hole 24 created by the drill 13 (FIG. 10) in the bone fragments 2, 3 for fixation of the bone fragments after locking also of this bone screw by a securing means 23.

In the preferred embodiment depicted, each securing means comprises a lock washer 23 with a peripheral thread and a central recess for a suitable screwing tool, e.g. the screwdriver 20. The lock washer 23 has preferably a thickness of about 3 mm. The respective securing means 23 may alternatively take the form of a locking screw (not depicted).

The configuration indicated of said second fixing portion 21 of the respective fixation means, the securing means 23 for it and the securing plate 4 therefore results in the fixation means being locked to the securing plate by the fact that the securing means, when screwed firmly into the respective, in the embodiment depicted, at least partly threaded hole 9 in the securing plate, presses the fixation means against the securing plate.

The result is a stable connection between the securing plate 4 and the bone screws 5, 6 which prevents the bone screws from changing their angular position relative to the plate and relative to one another in such a way that the bone screws would cross one another. There is also optimum fixation of the bone fragments 2, 3 by the bone screws 5, 6.

With the object of further improving the stability of the connection between the securing plate 4 and the bone screws 5, 6 and ensuring that the bone screws achieve correct orientation with the conically narrowing end portion 21 abutting correctly against the conically narrowing unthreaded portion 9b of the at least partly threaded hole 9 in the securing plate, so that when the lock washer 23 is screwed in, its peripheral thread achieves optimum engagement with the threaded portion 9a of the hole 9, the bone screws 5, 6, as also the lock washer 23 and the screwing tool, e.g. the screwdriver 20, may be cannulated, i.e. have a longitudinal duct, and may in this way also be guided by a guide wire 7 on which these items can be threaded so that the guide wire runs through the duct. Securing means 23 of some other type, e.g. locking screws, may of course also be cannulated.

However, the bone screws 5, 6 are also configured, as a result of their smooth middle portion 22, to allow the bone fragments 2, 3 to be compressed so that the outer bone fragment 2 slides inwards away from the securing plate 4 towards the inner bone fragment 3 into which the bone screws are firmly screwed. On such occasions, the securing plate 4 will, through being locked to the bone screws 5, 6 by the securing means 23, move away from its abutment against the outer bone fragment 2 (as represented schematically in FIG. 14 by the intermediate space 25 between the securing plate and the outer bone fragment), but without affecting the strength of the connection and without impairment of function.

As an alternative to the preferred embodiment depicted, the device according to the present invention may be provided with only one securing means 23, which in that case will be common to all the fixation means 5, 6. The holes 9 in the securing plate 4 will then not need to be threaded, at least not for locking of the fixation means, but may with advantage be replaced by a separate threaded hole (not depicted) for the securing means 23, situated centrally in the securing plate between the holes 9 for the fixation means. In that case all of the fixation means will be locked simultaneously by the securing means being screwed firmly into the threaded hole intended for it.

Figure 15:
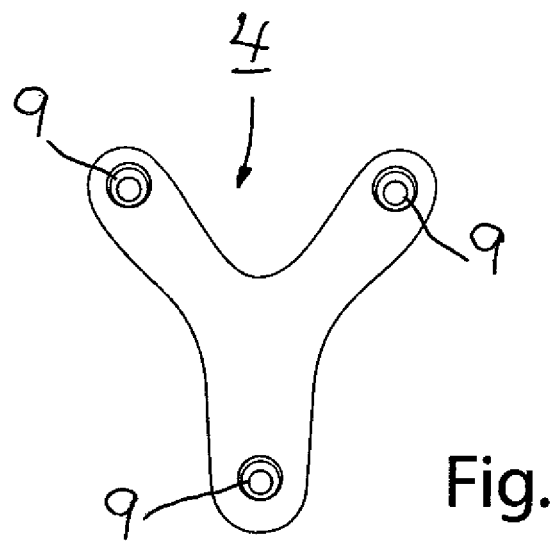
FIGS. 15 and 16 depict front views of two different alternative versions of the securing plate.
Figure 16:
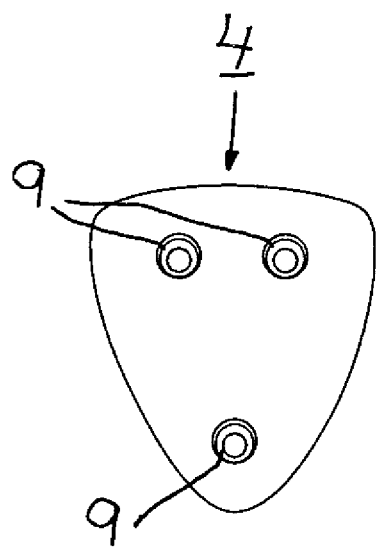

FIGS. 15 and 16 depict alternative versions of the securing plate 4. The securing plate 4 has in these versions three at least partly threaded holes 9 for bone screws, viz. two upper holes and one lower hole. The securing plate 4 may be configured in various sizes. For example, the securing plate 4 may be so configured that the distance between the upper holes 9 amounts to about 4.5, 6 or 7.5 mm, while the distance between the lower hole 9 and the respective upper holes 9 amounts to 6, 8 or 10 mm.

In all the versions depicted, the at least partly threaded holes 9 for the bone screws run substantially parallel with one another so that the bone screws 5, 6 will likewise run substantially parallel with one another. Parallel running of the fixation means facilitates in particular the sliding movement of the outer bone fragment 2 along the fixation means (along the middle portion 22 thereof) for compression of the bone fragments.

The securing plate 4 according to the present invention may be used not only for femur neck (collum) fractures but also for, for example, upper arm (humerus) fractures.

Since in operations for fixation of bone fragments at bone fractures it is important that the fixation means assume exactly predetermined positions relative to the bone fragments and to one another, it is of advantage that the device according to the invention also allows the application of guide sleeves for guidance of drills for drilling holes for the bone screws in the bone fragments, and/or guide sleeves for guidance of guide wires for said drills, in the same holes in the securing plate as are intended for the fixation means. This means that surgical staff need no longer keep count of an unnecessarily large number of different items for performing an operation, operating time becomes shorter and risks and complications for patients are reduced.

It will be obvious to one skilled in the art that the device according to the present invention can be modified and altered within the scope of the claims set out below without departing from the idea and objects of the invention. Thus, as indicated above, the securing plate 4 may be used for guide sleeves 8 for guide wires and thereafter for guide sleeves 11 for drills or, for example, immediately for guide sleeves 11 for drills. The securing plate 4 may of course also be used only for guide sleeves 8 for guide wires, followed by drill guidance solely by guide wire, without special guide sleeves for the drills. The securing plate 4 may also be used for bone screws of different kinds from the bone screws 5, 6 described above or for other types of fixation means, e.g. bone nails. A bone nail may have a sleeve and, disposed therein, a pin arranged for movement in the sleeve so that at least a forward portion of the pin can be driven outwards through at least one lateral aperture in the sleeve, in which case this forward portion constitutes a first fixing portion in the form of at least one hook which engages in the inner bone fragment, and the respective bone nail has in addition a second fixing portion of the type described above. As the density of the inner bone fragment is greatest at its centre, it is of advantage if the respective bone nail is applied in such a way that the forward portion of the pin is caused, during the driving, to engage in the central portions of the bone fragment. The respective bone nail may also be so configured as to achieve engagement in the central portions of the inner bone fragment. For example, where there is a threaded second fixing portion, the threads therein may be so disposed and/or configured that said result is achieved. Having the forward portion of the pin in the respective bone nail pointing towards the centre of the inner bone fragment not only means that the bone nails have a better grip in the inner bone fragment but also counteracts the risk of rotation or other movement of the bone nails. The size and choice of material of the constituent items of a surgical operating set may vary as necessary and desired.

The invention claimed is:
1. A device for fixation of bone fragments at bone fractures, wherein:
   the device comprises at least two fixation means, a securing plate and at least one securing means for the fixation means, the fixation means each have a first fixing portion for fixing the fixation means in an inner bone fragment, a second fixing portion to serve in conjunction with the securing means for locking the fixation means in a hole, the holes running through the securing plate disposed on the outside of an outer bone fragment without fixed connection with the outer bone fragment, the second fixing portion allowing movement of the outer bone fragment relative to the securing plate, so that the fixation means are prevented from changing an angular position relative to the securing plate and relative to one another, and a middle portion which is situated between the first and second fixing portions, the middle portion running through the outer bone fragment, the middle portion being configured to allow the outer bone fragment during compression after completion of surgery to slide inwards away from the securing plate and towards the inner bone fragment in which the fixation means are fixed, and at the same time, cease its abutment against the securing plate in which the fixation means are located, thereby defining a space between the outer bone fragment and the securing plate, and the securing means having an external thread screwed firmly into a hole in the securing plate, the second fixing portion of each fixation means includes an unthreaded rear end portion which narrows conically in the screwing-in direction of the fixation means, the at least partly threaded holes running through the securing plate include a corresponding conically narrowing unthreaded portion to receive the cone-shaped rear end portion of the respective fixation means, and the fixation means is locked to the securing plate as the securing means presses the conically narrowing end portion of the fixation means into abutment against the conically narrowing portion of the hole in the securing plate when the securing means is screwed firmly into the hole in the securing plate.

2. A device according to claim 1, wherein:

the device comprises the securing means for each fixation means, the hole in the securing plate for each fixation means is at least partly threaded, and the securing means is screwed firmly into the respective hole in the securing plate for each fixation means.

3. A device according to claim 2, wherein the securing plate is configured to allow screwing of guide sleeves to receive first and second drills to drill holes for the fixation means in the bone fragments, and/or guide sleeves to receive guide wires to guide one of the first and second drills during the drilling.

4. A device according to claim 3, wherein the threads of the at least partly threaded holes are configured to receive one or more of the guide sleeves and the securing means.

5. A device according to claim 1, wherein the securing means is a lock washer with a peripheral thread which cooperates with a threaded portion of the hole.

6. A device according to claim 5, wherein the lock washer has a central recess for a screwing tool.

7. A device according to claim 5, wherein the lock washer is cannulated to receive a guide wire during screwing of the lock washer into the hole in the securing plate.

8. A device according to claim 1, wherein the holes in the securing plate run substantially parallel with one another.

9. A device according to claim 1, wherein each fixation means is a bone screw with a first fixing portion having a threaded forward end portion.

10. A device according to claim 9, wherein the bone screw is cannulated to receive a guide wire during screwing of the bone screw into the inner bone fragment.

11. A device according to claim 1, wherein each fixation means is a bone nail which comprises a sleeve and a pin disposed within the sleeve, the pin being arranged for movement in the sleeve so that at least a forward portion of the pin is driven outwards through at least one lateral aperture in the sleeve, a forward portion of the pin includes a first fixing portion having at least one hook, the first fixing portion engaging in the inner bone fragment.

12. A device according to claim 11, wherein the bone nail is applied in a locking position with the lateral aperture of the sleeve directed inwards so that, during the driving of the pin, the forward portion of the pin engages the central portions of the inner bone fragment.

13. A device according to claim 12, wherein the second fixing portion of the bone nail is threaded, the threads therein being disposed and/or configured so that the lateral aperture of the sleeve is directed inwards after the bone nail has been applied in a locking position such that the forward portion of the pin engages the central portions of the inner bone fragment during the driving of the pin.

14. The device according to claim 1, wherein the device is used at femur neck (collum) fractures.

15. The device according to claim 1, wherein the device is used at upper arm (humerus) fractures.

16. The device of claim 1, wherein the securing means rests on a portion of the second fixing portion of the fixation means.

17. The device of claim 1, wherein the unthreaded, conically narrowing end portion of the fixation means engages the conically narrowing portion of the hole in the securing plate when the securing means is screwed firmly into the hole in the securing plate.

18. The device of claim 1, wherein the fixation means has an axial end surface facing away from the securing plate, the securing means abutting the axial end surface to push the conically narrowing end portion of the fixation means into the conically narrowing portion of the hole.

* * * * *